United States Patent
Davey (10) Patent No.: US 6,591,661 B2
(45) Date of Patent: Jul. 15, 2003

(54) APPARATUS AND METHOD FOR MEASUREMENT OF PERMEABILITY OR STRAIN IN PERMEABLE MATERIALS

(75) Inventor: Kenneth John Davey, Bassendean, WA (US)

(73) Assignee: Structural Monitoring Systems Ltd., West Perth (AU)

( * ) Notice: Subject to any disclaimer, the term of this patent is extended or adjusted under 35 U.S.C. 154(b) by 0 days.

(21) Appl. No.: 09/867,273

(22) Filed: May 29, 2001

(65) Prior Publication Data

US 2002/0038568 A1 Apr. 4, 2002

(30) Foreign Application Priority Data

May 30, 2000 (AU) ............................................. PQ7880

(51) Int. Cl.⁷ .......................... G01M 3/02; G01N 15/08
(52) U.S. Cl. ........................................................ 73/38
(58) Field of Search ......................... 73/37, 38, 152.41; G01M 3/02; G01N 15/08

(56) References Cited

U.S. PATENT DOCUMENTS

| | | | |
|---|---|---|---|
| 3,035,440 A | * | 5/1962 | Reed ........................ 73/152.41 |
| 3,918,291 A | | 11/1975 | Pauly et al. |
| 4,104,906 A | | 8/1978 | Oertle |
| 4,145,915 A | | 3/1979 | Oertle |
| 4,353,249 A | * | 10/1982 | Lagus et al. ............. 73/152.41 |
| 4,531,403 A | * | 7/1985 | de Korompay et al. ......... 73/38 |
| 4,651,557 A | | 3/1987 | Cholet |
| 4,776,206 A | | 10/1988 | Armstrong et al. |
| 4,854,157 A | * | 8/1989 | Wilson ........................... 73/38 |
| 4,979,390 A | | 12/1990 | Schupack et al. |
| 5,078,005 A | | 1/1992 | Krempel et al. |
| 5,205,173 A | | 4/1993 | Allen |
| 5,219,388 A | * | 6/1993 | Meletiou et al. ......... 73/152.31 |
| 5,404,747 A | | 4/1995 | Johnston et al. |
| 5,501,273 A | * | 3/1996 | Puri ........................... 166/252.5 |
| 5,544,520 A | | 8/1996 | Graf et al. |
| 5,596,137 A | | 1/1997 | Perry et al. |
| 5,770,794 A | * | 6/1998 | Davey ........................... 73/37 |
| 6,223,587 B1 | | 5/2001 | Chiocca |

FOREIGN PATENT DOCUMENTS

| | | |
|---|---|---|
| EP | 0 177 433 | 8/1985 |
| WO | 94/27130 | 11/1994 |

* cited by examiner

*Primary Examiner*—Helen Kwok
*Assistant Examiner*—Jay L Politzer
(74) *Attorney, Agent, or Firm*—Allen, Dyer, Doppelt, Milbrath & Gilchrist, P.A.

(57) ABSTRACT

Apparatus 10 for measuring permeability of a material 12 includes a substantially constant vacuum source 14 coupled via duct 11 to a fluid capacitance vessel 16 which contains pressure transducer 18 coupled by conductors 20 to an amplifier and display 22 for monitoring the source 14. Fluid impervious disc 24 is provided with placement on surface 26 on the material 12 to define, between disc 24 and surface 26 a fluid flow cavity 28. Disc 24 is coupled by conduit 32 to a restriction tube 30 which provides a high impedance to fluid flow. An opposite end of the restriction tube 30 is in fluid communication with vessel 16. A transducer 34 is coupled across restriction tube 30 to provide a measure of fluid flow. Fluid impervious seal 60 forms a seal about the periphery of disc 24 and extends radially outwardly on the surface 26. Assuming the material 12 has some degree of permeability, air will be able to permeate through the material 12 from beyond the periphery of the seal 60 and to the cavity 28. This flow produces a steady state of pressure differential across the tube 30 which is detected by transducer 34 and which can be read from display 38, to provide a measure of permeability.

10 Claims, 9 Drawing Sheets

APPARATUS AND METHOD FOR MEASUREMENT OF PERMEABILITY OR STRAIN IN PERMEABLE MATERIALS

FIELD OF THE INVENTION

The present invention relates to an apparatus and method for measurement of permeability or strain in permeable materials.

BACKGROUND OF THE INVENTION

Permeability of a material can be defined as a rate of which a fluid flows through the material. The measurement of the permeability of materials, for example concrete, is of importance in determining the suitability of the material for various purposes such as fluid containment and structural life. Changes in permeability with stress presents a method of measuring strain in permeable material.

Generally, the known methods of measurement of permeability measure a change in pressure of a gas applied to the material and/or depth of liquid penetration in the material. This method is known as the pulse test method. This method takes a substantial time to run and may involve the preparation of special samples. For example, the contemporary construction industry relies heavily on laboratory tests carried out on samples taken during a pour of a large concrete slab or structure to ascertain the strength of the concrete for further construction to be carried out. A steady state test method is a another, more desirable, method and is employed in the current specification. Further, the steady state test method is practical for the measurement of strain. In situ testing is a further desired attribute to reduce time taken and cost. U.S. Pat. No. 4,979,390 describes one method and apparatus for testing relative permeability of materials. In general terms, this requires the application of a partial vacuum to a small test area on a piece of concrete and measuring the rate of decay of the vacuum to provide an index of permeability. A limitation of the method and apparatus described is that it is restricted to a measurement of relative permeability and only a single test surface of relatively small area.

International Application No PCT/AU94/00325 (WO 94/27130) Tulip Bay discloses a monitoring apparatus that can be used to detect faults or cracks in the surface of or within a structure or component. The monitoring apparatus described includes a substantially constant vacuum source connected in series with a high impedance to fluid flow device that in turn is connected with one or more minuscule flaw sensing cavities formed on the surface of or within a structure. A differential pressure transducer is connected across the high impedance device to monitor the vacuum state of the minuscule flaw sensing cavity or cavities. A pressure differential transducer monitors the change in vacuum condition between the minuscule flaw sensing cavities and the constant vacuum source. Accordingly, if there is a change in vacuum condition in the cavities which can arise from the formation and propagation of a crack, the change is detected by the transducer. Cracks of a length down to 250 micron have been detected using a constant vacuum source of only 200 KpA below atmospheric reference.

The apparatus in Tulip Bay is particularly well suited to incorporation in embodiments of the present invention. Accordingly the contents of Tulip Bay are incorporated herein by way of reference.

SUMMARY OF THE INVENTION

It is an object of the present invention to provide a simple, low cost in situation, method and apparatus for providing a measurement of the permeability of a material. It is a further object to provide a means of method and apparatus for measuring strain in permeable material by means of change in permeability with applied stress.

According to the present invention there is provided an apparatus for providing a measure of the permeability of a material including at least:

a substantially constant fluid pressure source;

at least one fluid impervious means for juxtaposition with the material in a manner to define, between said means and said material a corresponding fluid flow cavity;

a high fluid flow impedance means providing high impedance fluid communication between said pressure source and said fluid flow cavity;

sealing means for juxtaposition with the material and the fluid impervious means to define a fluid impervious region between said fluid flow cavity and a free surface of the material; and, means for measuring steady state differential pressure across said high fluid flow impedance means to provide a measure of the permeability of said material.

Preferably said sealing means includes a seal that seals a peripheral edge of said article at a surface of said material and extends from the peripheral edge to define said fluid impervious region.

Preferably said at least one fluid impervious means includes a planar article for placement on said material.

Preferably said at least one fluid impervious means includes a sleeve disposed in a blind hole formed in the material, the sleeve extending for a portion of the length of the hole from the surface of the material and having a down-hole end spaced above a bottom of the hole, the sleeve forming a seal against an interior surface of said portion of the length of the hole, wherein said corresponding fluid flow cavity is defined between the down-hole end of the sleeve and the bottom of the hole.

Preferably said apparatus further includes a fluid impervious blank of a diameter less than the diameter of the hole and of a length less than a remainder of the length of the hole between said down-hole end of the sleeve and the bottom of the hole, said blank deposited in said hole prior to the insertion of said sleeve.

According to the present invention there is provided an apparatus for providing a measure of permeability of a material including at least:

a substantially constant fluid pressure source;

at least one first fluid impervious means each for placement on the material to define, between each first means and said material, a corresponding first fluid flow cavity;

first high fluid flow impedance means providing high impedance fluid communication between said pressure source and said first fluid flow cavities;

first sealing means for juxtaposition with the material and said first fluid impervious means to define respective fluid impervious regions between said first fluid flow cavities and a free surface of the material;

at least one second fluid impervious means each for placement in respective holes formed in said material in a manner to define, between said second means and a bottom of said holes, a corresponding second fluid flow cavities;

second high fluid flow impedance means providing high impedance fluid communication between said pressure source and said second fluid flow cavities;

second sealing means for juxtaposition with the material and the second fluid impervious means to define respective fluid impervious regions between said second fluid flow cavities and said free surface of the material; and means for measuring steady state differential pressure across said first and second high fluid flow impedance means to provide a measure of the permeability of said material.

According to the present invention there is also provided a method for obtaining a measure of the permeability of a material including at least the steps of:

providing a substantially constant fluid pressure source;

coupling said constant fluid pressure source through respective high fluid flow impedances to one or more fluid flow cavities formed on/or in the material;

forming respective fluid impervious seals on/or in the material about each fluid flow cavity to define corresponding fluid impervious regions between each fluid flow cavity and a free surface of the material; and, monitoring measuring steady state differential pressure across said high fluid flow impedances to provide a measure of permeability of the material.

According to the present invention there is also provided an apparatus for providing a measure of strain in a permeable material, said apparatus including at least:

a substantially constant fluid pressure source;

first and second fluid impervious means for juxtaposition at different locations with said material in a manner to define, between said means and said material, corresponding first and second fluid flow cavities;

first and second high fluid flow impedances providing high impedance fluid communication between respective first and second cavities and said pressure source;

said first cavity coupled in series at a first node to said first high fluid flow impedance, and said second cavity coupled in series at a second node to said second high fluid flow impedance;

sealing means for juxtaposition with the material and said first and second fluid impervious means to define a fluid impervious region between said first and second cavities and a free surface of said material; and, means for measuring steady state differential pressure across said first and second nodes to provide a measure of strain in said material.

According to a further aspect of the present invention there is provided a method of obtaining a measure of strain of a material, said method including at least the steps of:

providing a substantially constant fluid pressure source;

coupling said constant fluid pressure source through respective first and second high fluid flow impedances;

forming first and second fluid flow cavities on or in said material;

forming respective fluid impervious seals on/or in said material about said first and second fluid flow cavities to define corresponding fluid impervious regions between each of said fluid flow cavities and a free surface of said material;

coupling said first high fluid flow impedance in series at a first node to said first cavity;

coupling said second high fluid flow impedance in series at a second node to said second cavity; and measuring steady state pressure differential across said first and second nodes to provide a measure of strain in said material.

In one embodiment, said high impedance includes a very long length of small bore duct which allows a minuscule flow of fluid.

In an alternate embodiment, said high impedance comprises a permeable material such as sintered glass, an orifice or point restriction such as a needle valve being considered far too impracticable due to the minuscule flow required.

The magnitude of the high fluid flow impedance should be sufficiently high as to produce significant pressure drop across the high impedance in response to minuscule flow through the high impedance.

BRIEF DESCRIPTION OF THE DRAWINGS

Embodiments of the present invention will now be described by way of example only with reference to the accompanying drawings in which.

DETAILED DESCRIPTION OF PREFERRED EMBODIMENTS

Referring to FIGS. 1–3A, an embodiment of the apparatus 10, in accordance with the first part of the present invention, for providing a measure of the permeability of a material 12 includes a substantially constant fluid pressure source which, in this embodiment is in the form of a constant vacuum source 14 (a pressure source at a sub-atmospheric pressure). The vacuum source 14 is coupled via duct 11 to a fluid capacitance vessel 16 which contains a first pressure transducer 18 coupled by electrical conductors 20 to an amplifier and display 22 for monitoring the constant vacuum source 14. Throughout this specification the term "fluid pressure source" is intended to denote a source of fluid at any particular absolute pressure.

Figure 1:
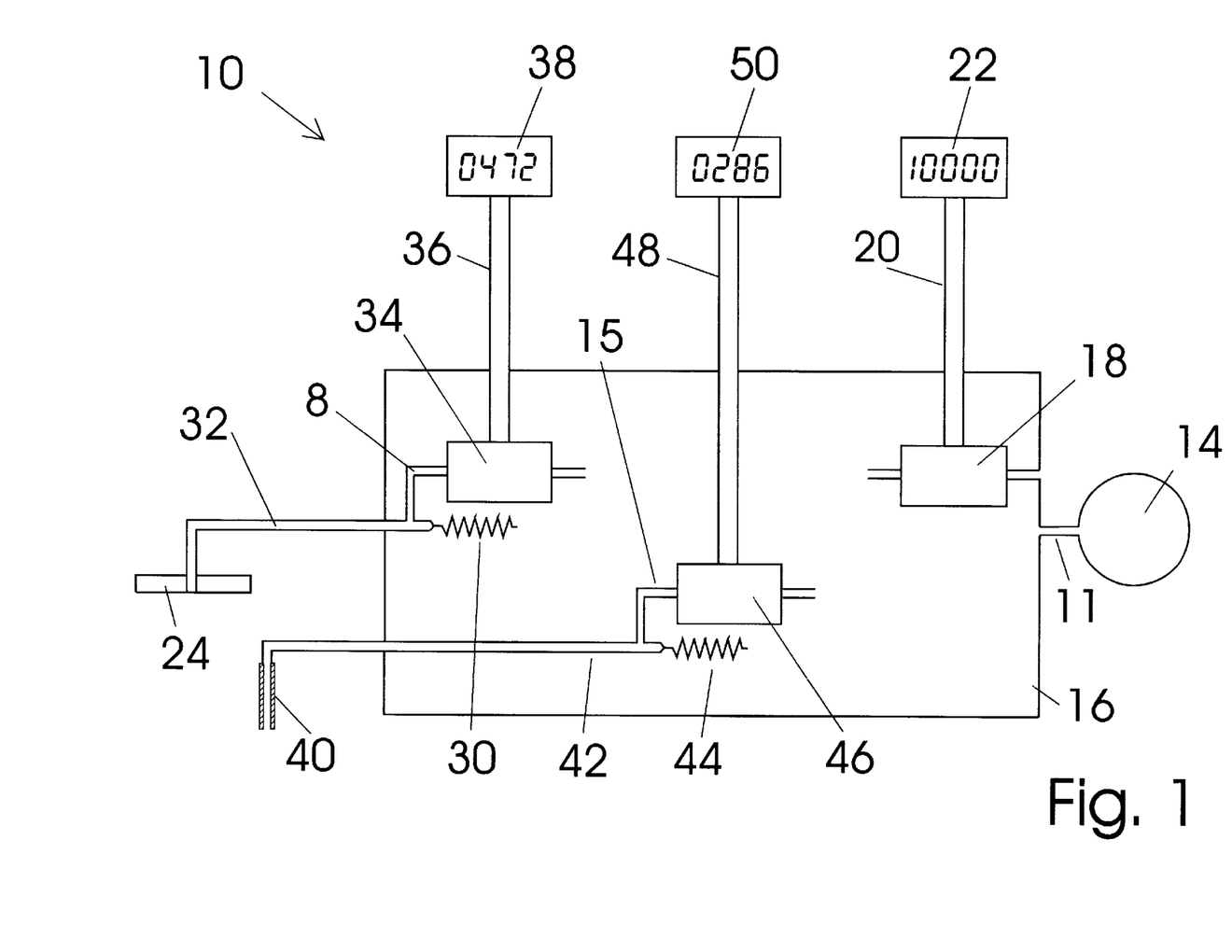
FIG. 1 is a schematic representation of an apparatus in accordance with the first part of the present invention.
Figure 2:
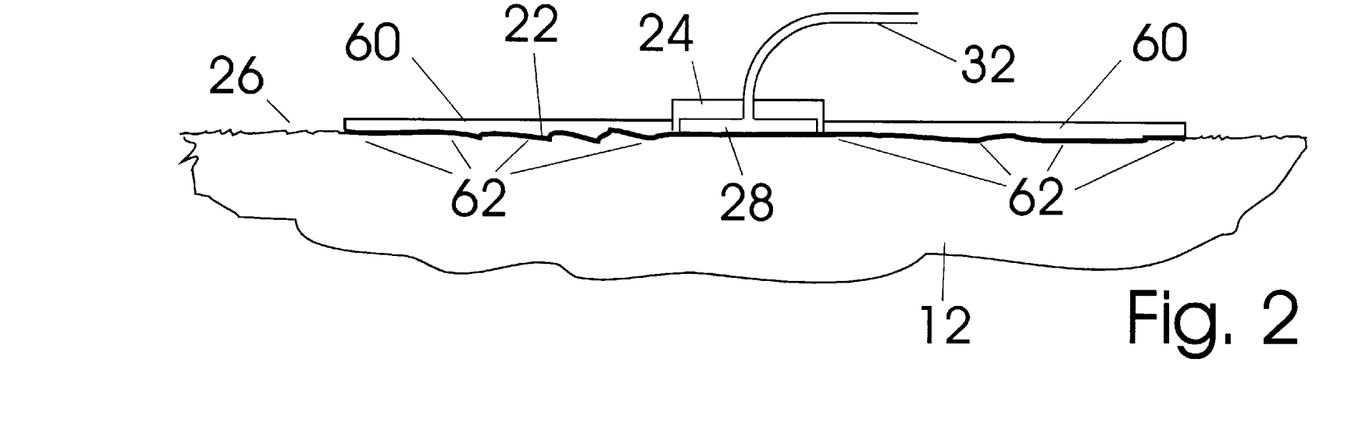
FIG. 2 is a schematic representation of an application of the apparatus of FIG. 1 for providing surface permeability measurement in a bulk material.

A first fluid impervious means in the form of a fluid impervious disc 24 is provided for placement on a surface 26 of the material 12 to define, between the disc 24 and the surface 26 a first fluid flow cavity 28 (see FIG. 2). The disc 24 is coupled to the vessel 16 and thus to the constant vacuum source 14 via a high impedance fluid flow means in the form of a length of a small bore duct such as restriction tube 30 (typical dimensions being less than 0.30 mm bore and length in excess of 3 meters). That is, one end of the impedance 30 is coupled to the vessel 16 with the other end coupled via a conduit 32 to the disc 24. A second pressure transducer 34 is coupled across the impedance 30 and coupled by conductors 36 to an amplifier and digital display 38.

A second fluid impervious means in the form of a sleeve 40 is coupled via a conduit 42 and high fluid flow impedance in the form of restriction tube 44 of the same dimensions as tube 30 to the vessel 16 and thus the constant vacuum source 14. Pressure transducer 46 is effectively coupled across the fluid impedance 44 between the sleeve 40 and the vacuum source 14. Additionally the transducer 46 is coupled by electrical conductors 48 to an amplifier and digital display 50.

The sleeve 40 is disposed in a blind hole 52 formed in the material 12. The sleeve 40 extends from the surface 26 of the material for a portion of the length of the hole 52 so that a down-hole end 54 is spaced from the bottom 56 of the hole 52. The sleeve 40 forms a seal against the interior surface of the portion of the hole 52 for which it extends (the gap shown between sleeve 40 and the interior surface of hole 52 in FIG. 3A is for clarity of illustration only, the gap does not actually exist). A fluid flow cavity 58 is defined between the down-hole end 54 of the sleeve and the bottom 56 of the hole. This cavity is placed in fluid communication with the vacuum source 14 by conduit 42 which couples to an axial bore 59 provided in the sleeve 40.

The cavities 28 and 58 are configured so that the surface area of the material under disc 24 in fluid communication with the vacuum source 14 is substantially the same as the surface area of the hole 52 between down-hole end 54 of the sleeve 40 and the bottom 56 of the hole 52, inclusive of the area of the bottom face of the hole 52.

Figure 5:
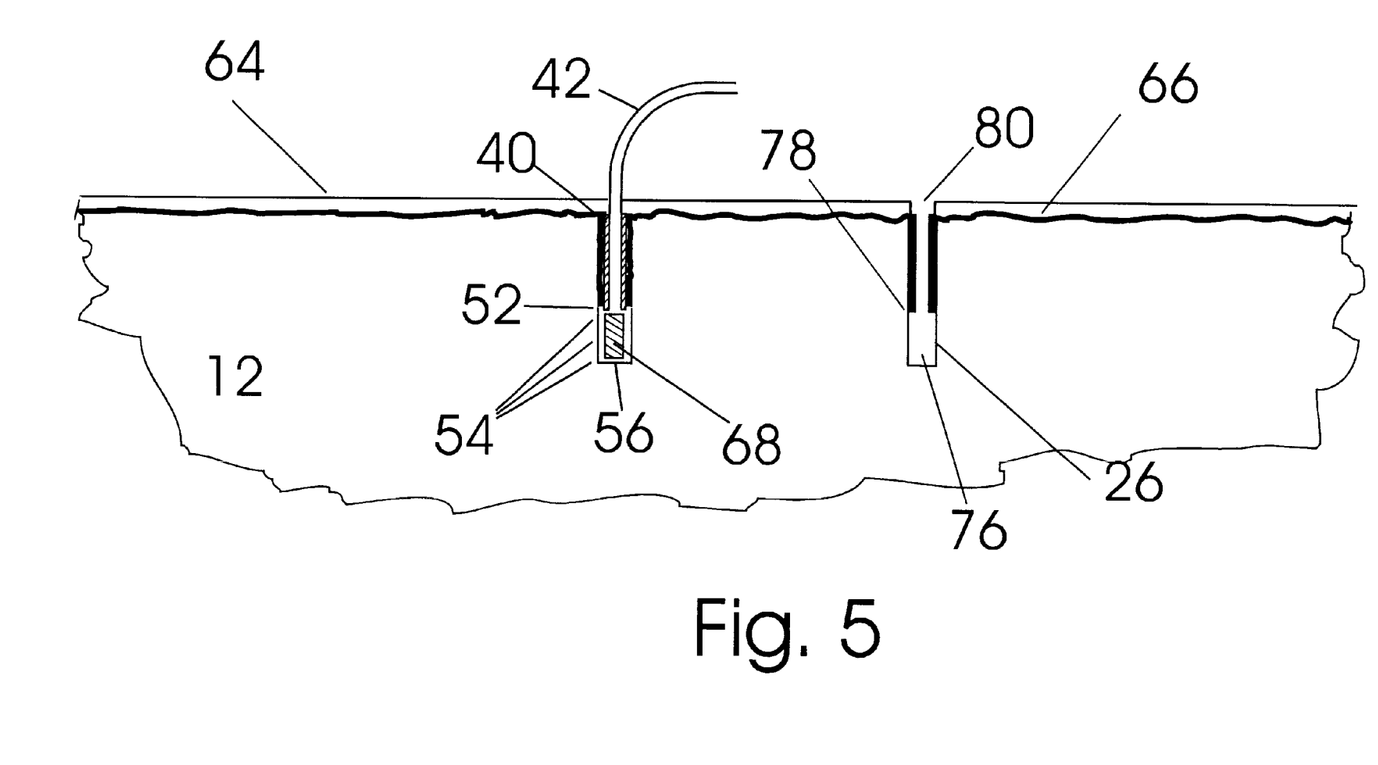
FIG. 5 is a schematic representation of an application of the apparatus of FIG. 1 for providing material to matrix permeability measurement in a bulk material.

Associated with the disc 24 and thus the first fluid flow cavity 28 is a fluid impervious seal 60. The seal 60 forms a seal about the periphery of the disc 24 and extends radially outwardly on the surface 26 of the material 12. The seal 60 thus forms on the surface 26 of the material a fluid impervious area or region 62 between the fluid flow cavity 28 and the "free surface" of the material 12. The term "free surface" refers to any surface of the material 12 that is open to fluid communication with the surrounding atmosphere/environment without third party impediment, this can include the surface of a hole or cavity formed in the material which is in fluid communication with the surrounding atmosphere/environment, (such as depicted in FIG. 5 as explained in greater detail below). A second fluid impervious seal in the form of a seal 64 forms a seal about the periphery of the sleeve 40 at surface 26 and extends radially outwardly on the surface 26 of the material 12. The seal 64 forms a fluid impervious area or region 66 between the fluid flow cavity 58 associated with the sleeve 40 and the free surface of the material 12 (refer FIGS. 3 and 3A), with the radial width of seals 60 and 64 being substantially the same.

When the apparatus 10 is applied to the material 12 it will be appreciated that after an initial transient period a constant (steady state) vacuum will exist in the fluid flow cavity 28 beneath disc 24 and the fluid flow cavity 58 beneath the sleeve 40. This creates a pressure differential between the cavities 28, 58 and the surrounding environment. Assuming that the material 12 has some degree of permeability, air is able to permeate through the material 12 from beyond the fluid impervious areas/regions 62, 66 to the fluid cavities 28, 58 respectively. This flow produces a steady state differential pressure across the corresponding high fluid impedance restriction tubes 30, 44 which will be displayed on corresponding displays 38 and 50. These displays can be directly calibrated into a scale of permeability. Accordingly the apparatus 10 can provide a measure of the specific permeability of the material 12. Particularly the apparatus 10 can provide either a measure of specific surface permeability via disc 28, of or specific matrix permeability via sleeve 40, or both.

In order to reduce the time for stabilisation of the vacuum state in the bottom of hole 52 at the initial application of the apparatus 10 when used to provide a measure of matrix permeability, a blank 68 can be provided for insertion into the hole 52 between the down-hole end 54 of the sleeve 40 and the bottom of 56 of the hole. The blank 68 is of a diameter less than that of the hole 52. The purpose of the blank 68 is simply to reduce the volume of the portion of the hole constituting the fluid flow cavity 58 thereby reducing the time required to evacuate the bottom of the hole prior to the commencement of the permeability measurement.

In order to produce highly accurate and meaningful results with repeatability, it is preferable to optimise the ratio of the fluid impervious areas or regions 62/66 with the surface areas of the material within cavities 28, 58. Take for example the arrangement shown in FIG. 2. If the fluid impervious area 62 is too small then a fluid flow path between the cavity 28 and the free surface of the material 26 will be too short to provide an accurate measurement of the permeability of the material. That is, there will not be sufficient fluid flow path length in the material 12 to provide an accurate reading of permeability. It is known however that after a certain distance or radius has been reached from the periphery of the cavity 28 there is insignificant difference in permeability measurement by extending the fluid impervious area 62. The ratio between the outer diameter of the area 62 and the cavity 28 can be found empirically for a particular material. 6:1 is a typically ratio. Additionally, it is preferable that the areas covered by the seals 60 and 64 are approximately the same.

In general application, a plurality of discs 24 and/or sleeves 40 with corresponding seals 60/64 can be arranged in line groups connected to one high fluid flow impedance or as simultaneous surface and matrix tests connected to two or more high fluid flow impedance restriction tubes. Of course the scale of impedance needs to be compensated if the use of multiple cavities alters the sum total exposed area of the cavities 28 and 58

Figure 3:
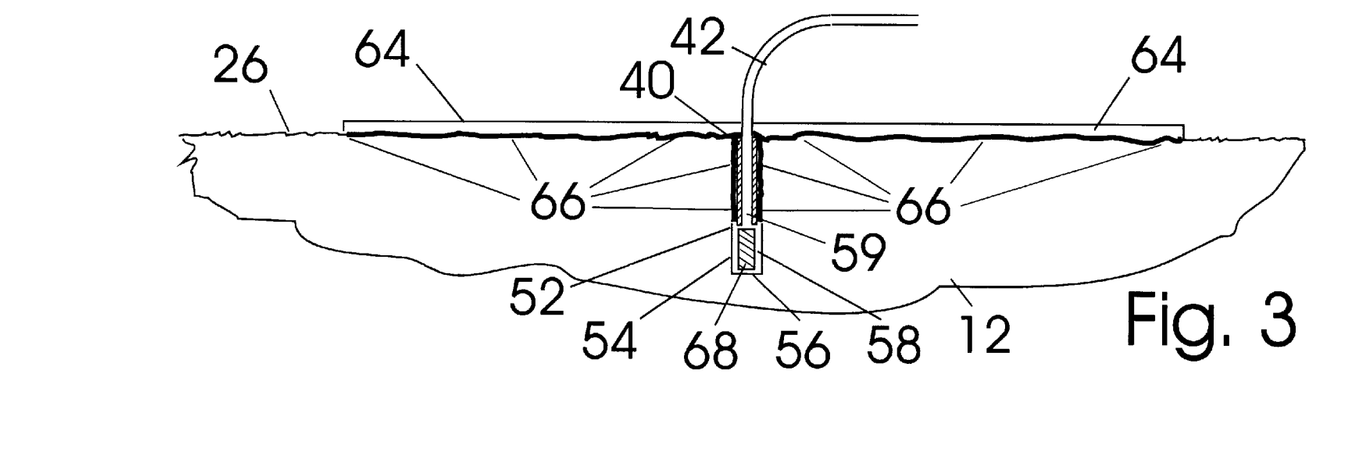
FIG. 3 is a schematic representation of an application of the apparatus of FIG. 1 for providing matrix to surface permeability measurement in a bulk material.
Figure 3A:
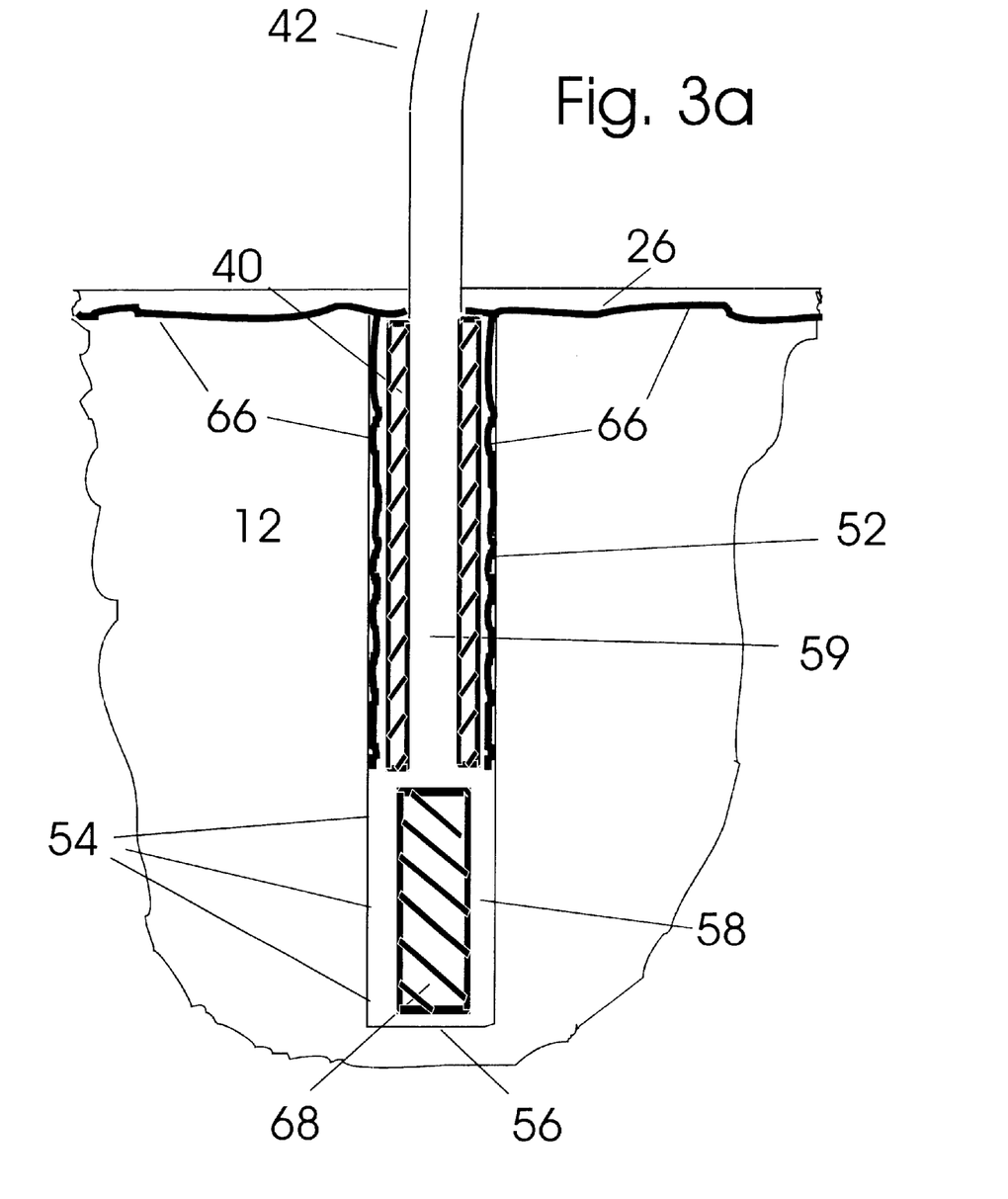
FIG. 3A is an enlargement of portion A of FIG. 3.

The apparatus depicted in FIG. 1 is configured to provide a measure of both surface to surface permeability of the bulk material 12 using the disk 24 as shown in FIG. 2 and surface to matrix permeability of the bulk material 12 using the sleeve 40 depicted in FIG. 3. It is however not essential that the apparatus 10 be configured to simultaneously take both surface to surface and surface to matrix permeability measurements. Either one of the high impedance restriction tubes 30 or 44 can be de-coupled so that the apparatus 10 takes the measurement of only surface to surface permeability or surface to matrix permeability of the bulk material 12.

As mentioned above, International Application No. PCT/AU94/00325 (Tulip) describes an monitoring apparatus particularly well suited for incorporation into embodiments of the present invention. With particular reference to FIG. 1, the impedances 30, 44, transducers 34, 46 and displays 30 and 50 may all take the form of that described in Tulip Bay. The particular advantage of incorporating the Tulip Bay apparatus is that it enables detection of fluid flow well below the lower limits of conventional mass flow meters. Further, if desired, the sensitivity of the apparatus can be increased infinitely by increasing the impedance of the high fluid flow impedances.

Figure 4:
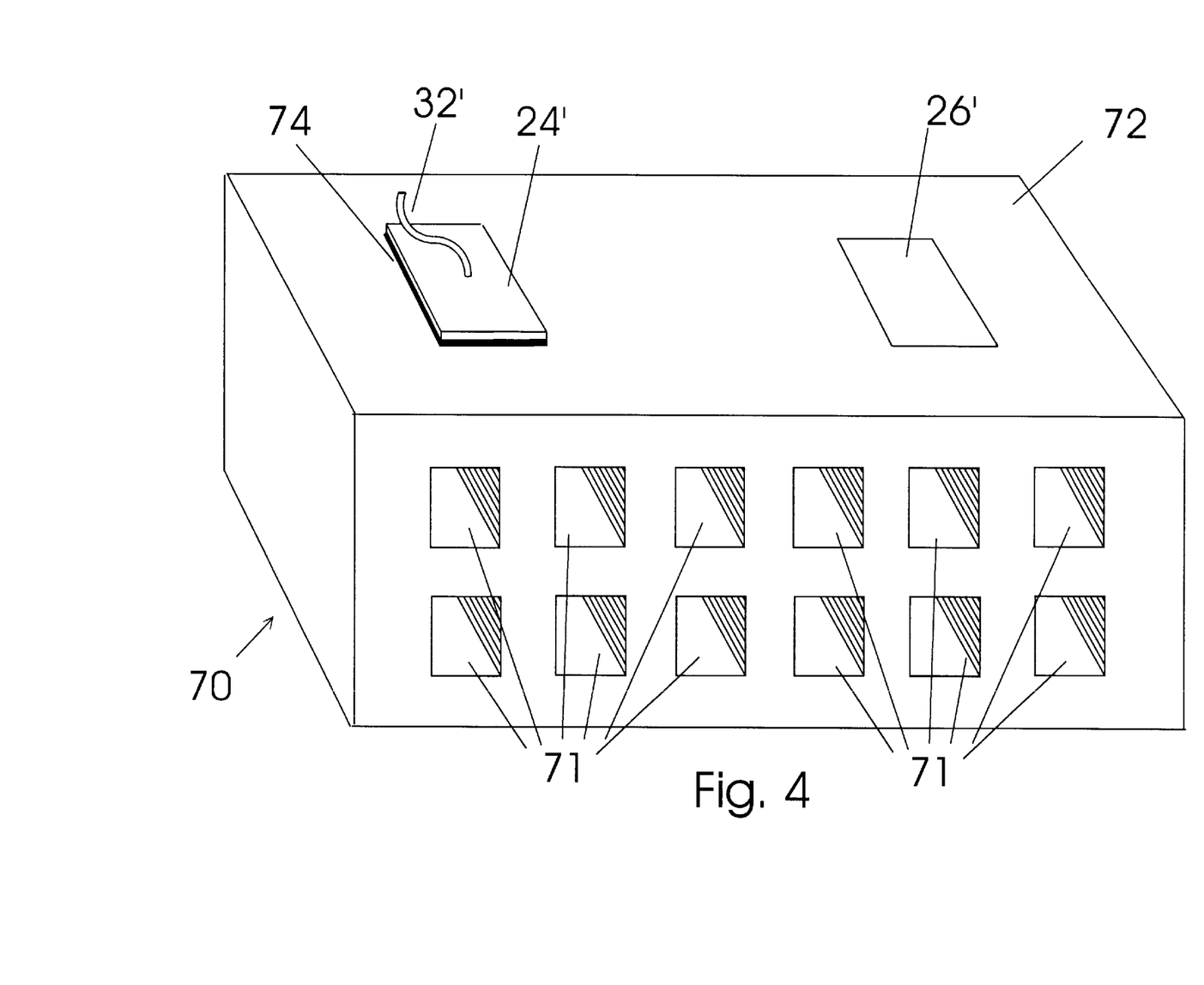
FIG. 4 is a schematic representation of an application of the apparatus of FIG. 1 for providing surface to surface permeability measurement in a sample of material.

Further to this, in a further application, the apparatus 10 can be configured, as illustrated in FIG. 4, to take surface to surface permeability measurement of a sample unit of material such as a brick 70. (In this embodiment the brick is illustrated as being provided with a plurality of apertures 71, but the provision of apertures is not necessary. The embodiment is equally applicable to a solid brick). In this application, a fluid impervious means in the form of a rectangular sheet 24' that is sealed to outer peripheral surface 72 of the brick 70 with a perimeter fillet of an adhesive 74. A corresponding cavity (hidden) is defined between the sheet 24' and the underlying area of the surface 72 of the brick 70. The cavity beneath the sheet 24' is in fluid communication with the high fluid impedance 30 via conduit 32', ie, in terms of FIG. 1, the disc 24 is replaced with the sheet 24'. The entirety of the remainder of the surface 72 of the brick 70 including the surface area of the apertures 71 but excluding a rectangular area 26' is sealed with a sealing compound. The area 26' is spaced a distance from the sheet 24' and is of the same area as the surface area of the brick 70 beneath the sheet 24' which is in fluid communication with the vacuum source 14. The operation of the apparatus 10 in the embodiment shown in FIG. 4 allows a measure of the permeability of a surface layer of the brick 70 between sheet 24' and area 26'.

FIG. 5 illustrates a configuration for making matrix to matrix permeability measurement in a bulk material 12. In comparison to the apparatus 10 depicted in FIG. 1 and the arrangement in FIG. 3, the configuration in FIG. 5 differs in that the disc 24 is not used, the free surface 26 is the surface area of a lower part 76 of a hole 78 formed in the bulk material 12 and, the seal 64 seals a greater surface area of the material 12. In this regard, the seal 64 extends along the surface of the material 12 from the sleeve 40 for a distance substantially greater than the distance between holes 52 and 78. Also, the seal 64 extends for a portion of the length of the hole 78 to the lower portion 76. However, the seal 64 does not completely block the hole 78 and a communication channel 80 is left or otherwise formed to allow fluid communication between the surface 26 of the bottom portion of the hole 76 and the atmosphere. The area of the surface 26 is approximately the same as the surface area of the hole 52 beneath the down-hole end 54 of the sleeve 40.

Of course matrix to matrix permeability measurement of a sample of material could be conducted using substantially the same configuration of apparatus depicted in FIG. 5, the only additional requirement is that either the seal 64 or another seal or sealing compound would seal the whole surface of the sample in a similar manner as described in relation to and as illustrated in FIG. 4.

In the above described embodiments, the constant fluid pressure source 10 has been described as a vacuum source. However the source can be a liquid such as water at a substantially constant pressure. This allows measurement of water permeability of the material 12. In such an application, the impedance of restrictive tubes 30 and 44 must be greatly increased to improve sensitivity to the reduction in the permeating fluid flow rate of water with respect to air. Typically, a length of a nominal 30 meters would be required to measure permeability rates of less than $1 \times 10^{-11}$ meters per second Measurements made in accordance with the second embodiment depicted in FIG. 4 may not directly relate to measurements in accordance with the set-up shown in FIGS. 2 and 3 unless empirical determination of the required tests surface and atmospheric venting surface dimensions at a distance between said surfaces is obtained.

Figure 6:
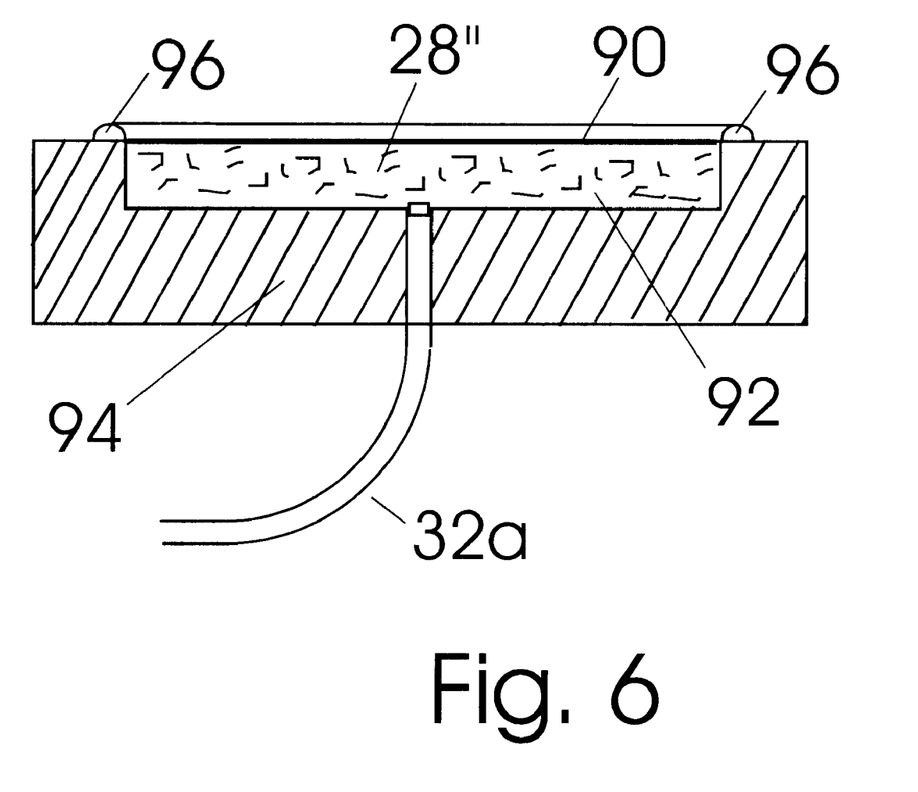
FIG. 6 illustrates application of the apparatus of FIG. 1 for measurement of the permeability of a paint film.

FIG. 6 illustrates application of the apparatus of FIG. 1 for measurement of the permeability of a paint film. A sectional view shows a paint film 90 that has been prepared by coating onto a surface which has subsequently been dissolved. The film 90 is then laid onto a freely permeable support medium 92 contained within a fluid impervious means in the form of an impermeable receptacle 94 and peripherally sealed (96) to the receptacle 94 by a peripheral seal 96. Here, a fluid flow cavity 28" is defined between the paint film 90 and the receptacle 94 by the medium 92. Duct 32a provides fluid communication to the apparatus 10 of FIG. 1 between cavity 28" and the constant vacuum source 14 of FIG. 1, in a similar way to duct 32, via a corresponding high fluid impedance and transducer. The film permeability can now be determined and the effects of environmental exposure can be compared at intervals for degradation.

Figure 7:
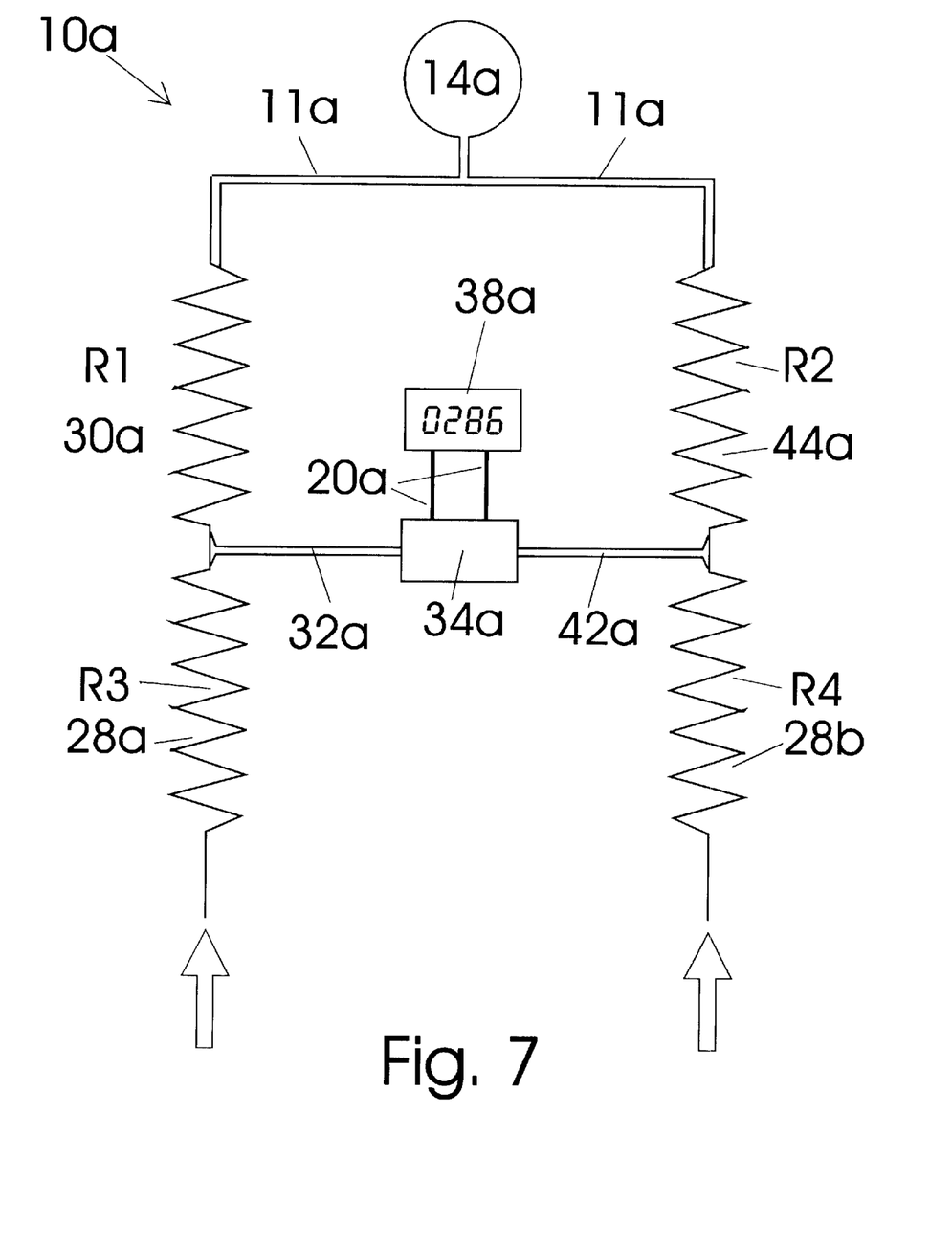
FIG. 7 is a schematic representation of an apparatus in accordance with a second aspect of the present invention.

FIG. 7 is a schematic representation of an apparatus in accordance with a further embodiment of the present invention for measuring strain in permeable material. Referring to FIGS. 1 and 7, the fluid capacitance vessel 16 has been removed for clarity. The vessel 16 normally serves as a convenient containment of components and smoothes pulsation that may evolve from the constant vacuum source 14. It will be obvious that by connecting duct 11 of FIG. 1 to the pressure transducers 18, 34, and 46, and the high fluid impedance tubes 30 and 44, the vessel 16 is redundant and simplifies FIG. 7.

The drawing of FIG. 7 has been arranged to represent a system 10a which is a fluid analogy of the familiar wheatstone bridge. In particular, it resembles a strain gauge half bridge in which two "permeability actuated" analogous strain gauges R3 and R4 are employed.

Figure 8:
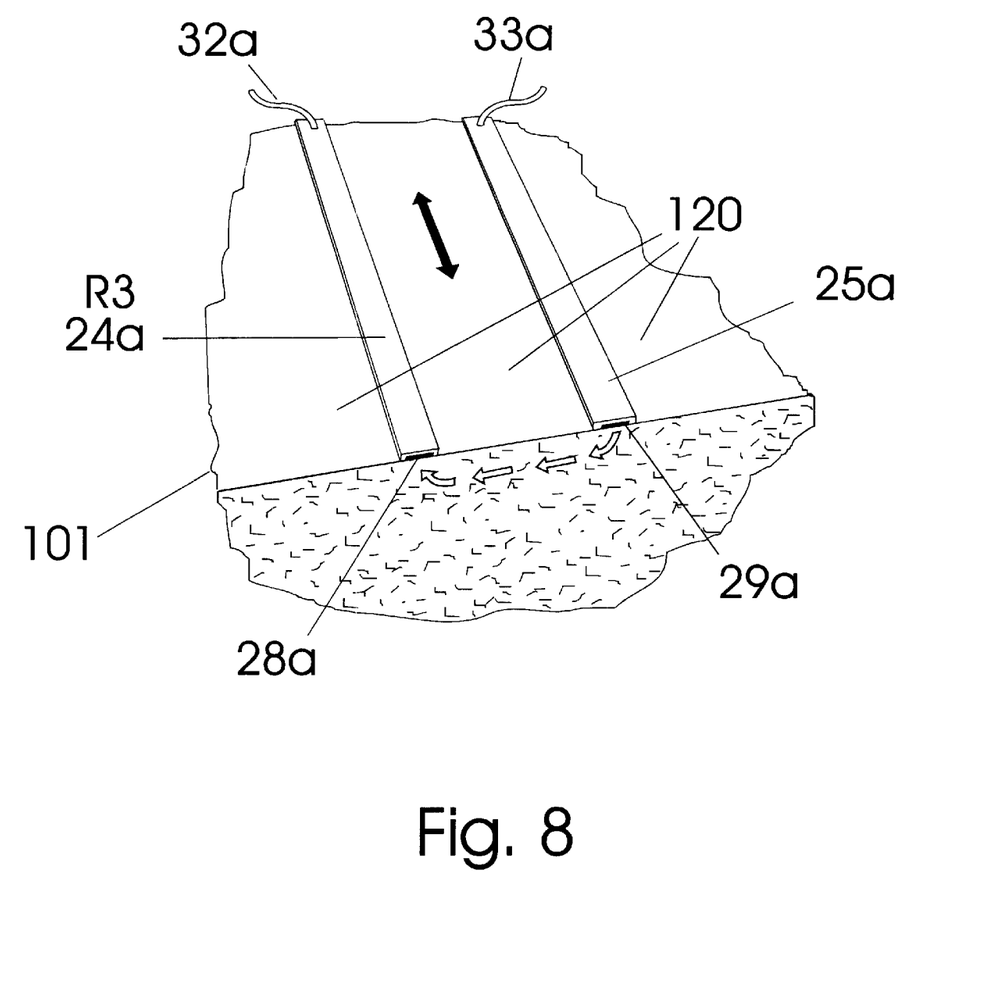
FIG. 8 is a schematic representation of a portion of the embodiment depicted in FIG. 7;and, FIG. 9 is a schematic representation of an application of the embodiment shown in FIG. 7.
Figure 9:
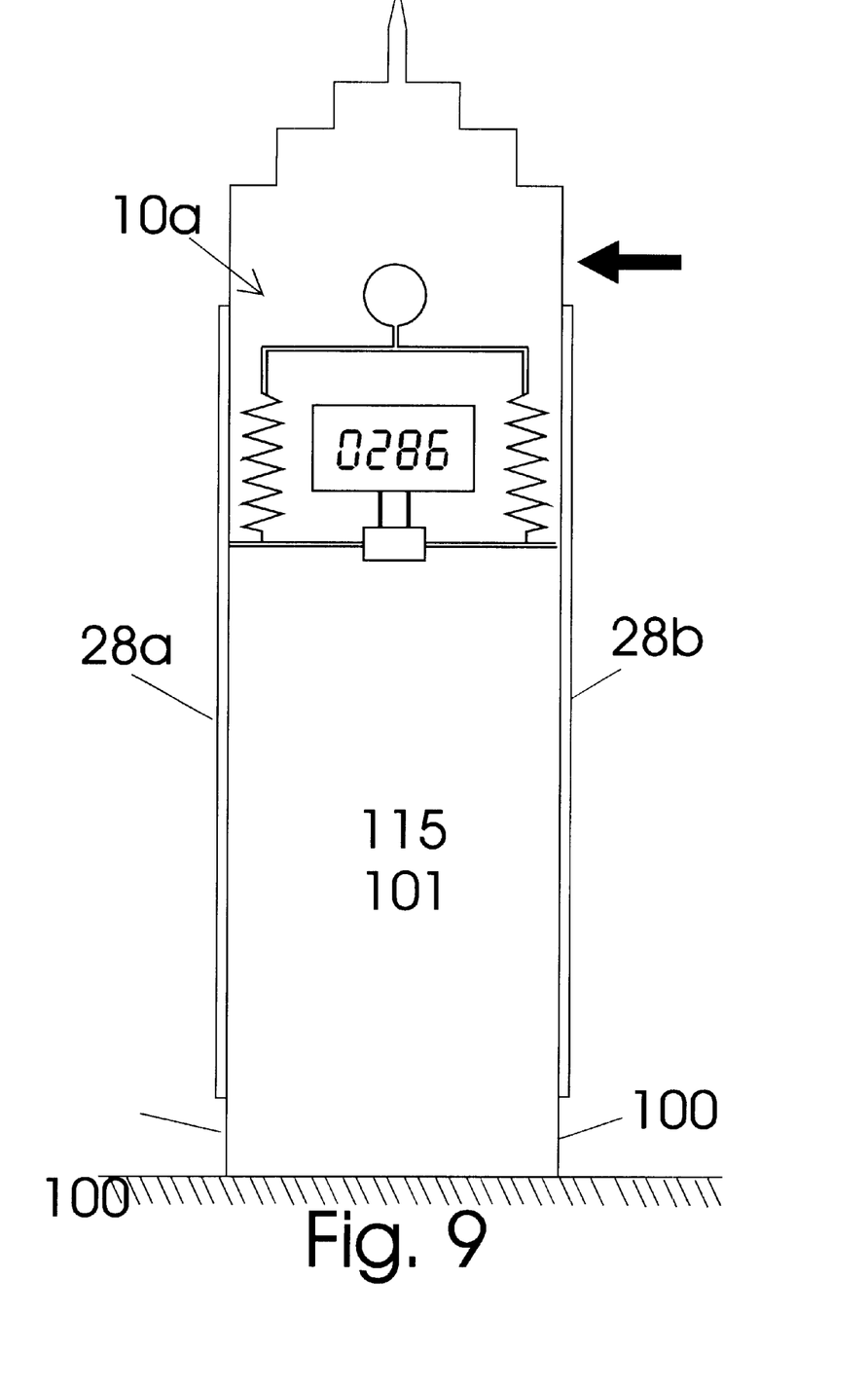

Referring to FIGS. 7, 8 and 9, a constant vacuum source 14a is connected via duct 11a to high fluid impedance tubes 30a and 44a (R1 and R2), thence to two cavities 28a and 28b respectively, formed on a surface 100 of a test substrate 101. The R3 and R4 resistor symbols represent resistance to atmospheric air permeation through the material 101 being investigated, into the cavities 28a and 28b. The atmospheric air ingress into the cavities 28a and 28b, against the resistance of the test material 101, is represented by the white arrow heads.

Similar to a strain gauge installation the cavities 28a and 28d respond to elongation or compression of a test surface to which they are attached. Unlike strain gauges wherein a change in electrical resistance occurs, the cavities experience a change in vacuum condition due to a change in the permeability of the test material 101 partly defining the cavities 28a and 28b. In like manner to strain gauges in a half bridge configuration, one cavity is attached to a surface undergoing tensile loading whilst the other is attached to a surface undergoing compressive loading.

In a further analogy to a strain gauge installation, a pressure difference is measured across a differential pressure transducer 34a fluidly connected by ducts 32a and 42a to the R1/R3 and R2/R4 junctions respectively. Conductors 20a provide electrical connection to an amplifier and display 38a. In order to achieve bridge balance under no load, the high fluid impedance tubes 30a and 44a (R1 and R2) can be made adjustable. This can be facilitated by spiral winding the tubes and containing between adjustable pressure plates. Alternatively, one such adjustable device can be placed as a series connection as appropriate with one of the cavity connections to duct 32a or 42a FIG. 8 shows detail of a typical cavity performing a function analogous with a strain gauge, for example, representing 28a (R3) of FIG. 7. A portion of concrete 101 has been sectioned to reveal a cavity 28a defined under an elongate strip of impermeable material 24a sealed peripherally to the concrete 101 by a surface coat of a fluid impermeable seal 120. Similarly, a second elongate strip of impermeable material 25a defines a cavity 29a and is arranged at a predetermined parallel distance from 24a/28a. The cavity 29a serves as a weather proof atmospheric reference being fluidly connected to atmosphere via duct 33a. The cavity 24a is fluidly communicated via duct 32a to the remainder of the system 10a of FIG. 7 and hence is connected to the vacuum source 14a.

With specific reference to FIG. 8, a permeable air flow varying in response to a varying stress, indicated by the black arrow, is illustrated by the white arrows. The flow is shown between the atmospheric cavity 29a and the vacuum cavity 28a. Micro-cracks in the surface of the concrete 101 open and close with variation in applied stress to produce this effect. The fluid impermeable seal 120 is extended sufficiently to provide weather protection, especially from rain.

FIG. 9 shows application of the system 10a to a high rise building 115 constructed of concrete (101).

Cavities 28a and 28b are attached to surfaces 100 on the sides of the building as viewed to measure strain due to a force, represented by a black arrow, produced for example by wind loading.

A correction to gas permeability measurement due to moisture content in concrete can be provided. This can be achieved directly by electrical conductivity measurement. Alternatively, by measuring the amount of water in the minuscule airflow over a predetermined time, a correction may be derived from a method such as chemical absorption, or a device wherein minuscule capacitor plates are chilled to collect moisture and alter capacitance and hence frequency in an electronic oscillator circuit.

Now that embodiments of the present invention have been described in detail it will be apparent to those skilled in the relevant arts that numerous modification and variations may be made without departing from the basic inventive concepts. For example, the apparatus shown in FIG. 1 depicts the use of a single disc 24 for providing surface permeability and a single sleeve 40 for providing matrix permeability. However multiple discs 24 and/or sleeves 40 can be incorporated in order to test large areas of material and/or to provide both surface permeability and matrix permeability measurements.

In another variation, permeability measurement of a layer of concrete at a selected depth may be accomplished by providing two elements of the configuration of FIG. 3 to produce a fluid flow, one to the other, and having all significant surfaces sealed.

Further, the inclusion of the vessel 16 is not essential and largely determined by the capacity of the constant pressure source.

With respect to strain measurement, liquid instead of gas may be appropriate such as in submerged applications. Further, in the embodiments depicted in FIGS. 7–9, the cavities formed on the material for which the strain is measured are illustrated as being formed on the surface of the material. However in a similar manner as illustrated in FIGS. 3 and 3a, the cavities can be formed internally of the material.

All such modifications and variations together with others that would be obvious to a person of ordinary skill in the art are deemed to be within the scope of the present invention the nature of which is to be determined by the above description, and the appended claims.

The claims defining the invention are as follows:

1. An apparatus for providing a measure of the permeability of a material including at least:
    a substantially constant fluid pressure source;
    a first fluid impervious member for juxtaposition and sealing with the material in order to define, between said first member and said material a corresponding first fluid flow cavity;
    a first high fluid flow impedance providing high impedance fluid communication between said pressure source and said first fluid flow cavity;
    a first seal for sealing an area of a surface of the material surrounding the first fluid impervious member to define a first fluid impervious region between said first fluid flow cavity and a free unsealed surface of said material; and
    a measuring device for measuring steady state differential pressure across said first high fluid flow impedance to provide a measure of the permeability of said material.

2. The apparatus according to claim 1, wherein said first fluid impervious member includes a planar article for placement on said material.

3. The apparatus according to claim 1, wherein said first fluid impervious member includes a sleeve disposed in a blind hole formed in the material, the sleeve extending for a portion of the length of the hole from the surface of the material and having a down-hole end spaced above a bottom of the hole, the sleeve forming a seal against an interior surface of said portion of the length of the hole, wherein said corresponding first fluid flow cavity is defined between the down-hole end of the sleeve and the bottom of the hole.

4. The apparatus according to claim 3 further including a fluid impervious blank of a diameter less than the diameter of the hole and of a length less than a remainder of the length of the hole between said down-hole end of the sleeve and the bottom of the hole, said blank deposited in said hole prior to the insertion of said sleeve.

5. An apparatus according to claim 1, wherein said first fluid impervious member is placed on the material to define said first fluid flow cavity; and further including:
    a second fluid impervious device for sealed placement in a blind hole formed in said material in a manner to define, between said second fluid impervious member and a bottom of said hole, a second fluid flow cavity;
    a second high fluid flow impedance providing high impedance fluid communication between said pressure source and said second fluid flow cavity;
    a second seal for sealing an area of the surface of the material surrounding said second fluid impervious member to define a second fluid impervious region between said second fluid flow cavity and said free unsealed surface of said material;
    wherein said measuring device measures steady state differential pressure across said first and second high fluid flow impedances.

6. A method for obtaining a measure of the permeability of a material including at least the steps of:
    providing a substantially constant fluid pressure source;
    coupling said constant fluid pressure source through a first high fluid flow impedance to a first fluid flow cavity formed on or in the material;

forming a first fluid impervious seal on or in the material about said first fluid flow cavity to define the first fluid flow cavity;

sealing an area of a surface of the material surrounding the first fluid impervious seal to define a first fluid impervious region between the first fluid flow cavity and a free unsealed surface of said material; and measuring steady state differential pressure across said first high fluid flow impedance to provide a measure of permeability of the material.

7. An apparatus according to claim 1 further including:

a second fluid impervious member spaced from said first fluid impervious means, said second fluid impervious member juxtaposed with and sealed to said material in a manner to define, between said second fluid impervious member and said material, a second fluid flow cavity;

a second high fluid flow impedance providing high impedance fluid communication between said second cavity and said pressure source; said first cavity coupled in series at a first node to said first high fluid flow impedance and said second cavity coupled in series at a second node to said second high fluid flow impedance;

said sealing means being juxtaposed with said material and said first and second fluid impervious members whereby said fluid impervious region extends between said first and second cavities and said free unsealed surface of said material; and said measuring device being coupled to both said first and second high fluid flow impedances and said first and second nodes respectively to provide a measure of a difference in permeability of said material between said first cavity and said free surface, and between said second cavity and said free surface.

8. A method according to claim 6 including the steps of:

forming a second fluid flow cavity on or in said material;

coupling said constant fluid pressure source through a second high fluid flow impedance to said second fluid flow cavity;

forming a second fluid impervious seal on or in said material about said second fluid flow cavity to define a second fluid impervious region between said second fluid flow cavity and said free unsealed surface of said material;

coupling said first high fluid flow impedance in series at a first node to said first cavity;

coupling said second fluid flow impedance in series at a second node to said second cavity; and measuring steady state pressure differential across said first and second nodes.

9. An apparatus for providing a measure of the difference in permeability between surfaces of a permeable material subjected to a load, said apparatus including:

a substantially constant fluid pressure source;

first and second fluid impervious means for juxtaposition at different locations with said material in a manner to define, between said means and said material, corresponding first and second fluid flow cavities;

first and second high fluid flow impedances providing high impedance fluid communication between respective first and second cavities and said pressure source; said first cavity coupled in series at a first node to said first high fluid flow impedance, and said second cavity coupled in series at a second node to said second high fluid flow impedance;

sealing means for juxtaposition with the material and said first and second fluid impervious means to define a fluid impervious region between said first and second cavities and a free surface of said material; and means for measuring steady state differential pressure across said first and second nodes.

10. A method of obtaining a measure of the difference in permeability between surfaces of a permeable material subjected to a load, said method including the steps of:

providing a substantially constant fluid pressure source;

coupling said constant fluid pressure source to first and second fluid flow cavities formed on or in said material through respective first and second high fluid flow impedances;

forming the first and second fluid flow cavities with respective fluid impervious members on/or in said material;

sealing an area of a surface of the material surrounding the first and the second fluid impervious members to define a first and a second fluid impervious region between the first and the second fluid flow cavity and a free unsealed surface of said material;

coupling said first high fluid flow impedance in series at a first node to said first cavity;

coupling said second high fluid flow impedance in series at a second node to said second cavity; and measuring steady state pressure differential across said first and second nodes.

* * * * *